(12) United States Patent
Star-Lack et al.

(10) Patent No.: US 9,400,332 B2
(45) Date of Patent: Jul. 26, 2016

(54) MULTI-ENERGY X-RAY IMAGING

(71) Applicants: VARIAN MEDICAL SYSTEMS, INC., Palo Alto, CA (US); VARIAN MEDICAL SYSTEMS INTERNATIONAL AG

(72) Inventors: Josh Star-Lack, Palo Alto, CA (US); Michael Green, Palo Alto, CA (US); Heinrich Riem, Baden-Daettwil (CH); Timothy Guertin, Saratoga, CA (US)

(73) Assignees: VARIAN MEDICAL SYSTEMS INTERNATIONAL AG, Zug (CH); VARIAN MEDICAL SYSTEMS, INC., Palo Alto, CA (US)

( * ) Notice: Subject to any disclaimer, the term of this patent is extended or adjusted under 35 U.S.C. 154(b) by 7 days.

(21) Appl. No.: 14/139,283

(22) Filed: Dec. 23, 2013

(65) Prior Publication Data
US 2014/0110594 A1    Apr. 24, 2014

Related U.S. Application Data

(62) Division of application No. 12/123,380, filed on May 19, 2008, now Pat. No. 8,633,445.

(51) Int. Cl.
*G21K 1/02* (2006.01)
*G01T 1/16* (2006.01)
(Continued)

(52) U.S. Cl.
CPC . *G01T 1/16* (2013.01); *A61B 6/032* (2013.01); *A61B 6/12* (2013.01); *A61B 6/4014* (2013.01);
(Continued)

(58) Field of Classification Search
CPC .... A61B 6/032; A61B 6/4035; A61B 6/4441; A61B 6/542; A61B 6/4233; A61B 6/5282; A61B 6/4014; A61B 6/469; A61B 6/5205; A61B 6/5235; A61B 6/585; G01T 1/16; A61N 2005/1054
USPC ...................................................... 250/363.1
See application file for complete search history.

(56) References Cited

U.S. PATENT DOCUMENTS 4,382,208 A    5/1983   Meddaugh et al.
4,792,900 A *  12/1988  Sones ................. A61B 6/4241
                                                378/98.9
(Continued)

OTHER PUBLICATIONS

Final Office Action for U.S. Appl. No. 12/123,380 mailed on May 21, 2013, 14 pages.
(Continued)

*Primary Examiner* — David J Makiya
*Assistant Examiner* — Taeho Jo
(74) *Attorney, Agent, or Firm* — Vista IP Law Group, LLP; Gerald Chan

(57) ABSTRACT

An imaging method includes obtaining a first image data for a subset of a target region, the subset of the target region having a first metallic object, obtaining a second image data for the target region, and using the first and second image data to determine a composite image. A imaging system includes a first detector configured to provide a first projection data using a first radiation having high energy, and a second detector configured to provide a second projection data using a second radiation having low energy, wherein the first detector has a first length, the second detector has a second length, and the first length is less than 75% of the second length.

31 Claims, 12 Drawing Sheets

(51) Int. Cl.
*A61B 6/03* (2006.01)
*A61B 6/12* (2006.01)
*A61B 6/00* (2006.01)
*A61B 6/06* (2006.01)
*A61N 5/10* (2006.01)

(52) U.S. Cl.
CPC ............ *A61B 6/4035* (2013.01); *A61B 6/4233* (2013.01); *A61B 6/4441* (2013.01); *A61B 6/469* (2013.01); *A61B 6/482* (2013.01); *A61B 6/5205* (2013.01); *A61B 6/5235* (2013.01); *A61B 6/5282* (2013.01); *A61B 6/542* (2013.01); *A61B 6/585* (2013.01); *A61B 6/06* (2013.01); *A61N 2005/1054* (2013.01)

(56) References Cited

U.S. PATENT DOCUMENTS

| | | | | |
|---|---|---|---|---|
| 5,432,334 A * | | 7/1995 | Nelson | G01T 1/2018 250/208.1 |
| 5,442,672 A * | | 8/1995 | Bjorkholm | G01N 23/046 378/4 |
| 5,548,123 A * | | 8/1996 | Perez-Mendez | G01T 1/2018 250/370.09 |
| 5,648,997 A * | | 7/1997 | Chao | A61B 6/06 378/147 |
| 5,771,269 A * | | 6/1998 | Chao | A61B 6/06 378/147 |
| 6,041,097 A | | 3/2000 | Roos et al. | |
| 6,052,433 A * | | 4/2000 | Chao | A61B 6/06 378/147 |
| 6,366,021 B1 | | 4/2002 | Meddaugh et al. | |
| 6,864,633 B2 | | 3/2005 | Trail et al. | |
| 7,324,623 B2 * | | 1/2008 | Heuscher | A61B 6/032 378/16 |
| 7,339,320 B1 | | 3/2008 | Meddaugh et al. | |
| 7,400,093 B2 | | 7/2008 | Salop et al. | |
| 7,400,094 B2 | | 7/2008 | Meddaugh | |
| 7,432,672 B2 | | 10/2008 | Meddaugh et al. | |
| 7,657,000 B2 * | | 2/2010 | Hirshenbein | G01N 23/04 378/98.11 |
| 8,144,829 B2 * | | 3/2012 | Zhu | A61B 6/032 378/7 |
| 8,440,978 B2 * | | 5/2013 | Morf | 250/370.09 |
| 8,633,445 B2 | | 1/2014 | Star-lack et al. | |
| 2002/0149305 A1 * | | 10/2002 | Danielsson | A61N 5/1048 313/105 CM |
| 2002/0168046 A1 * | | 11/2002 | Hansen | G01N 23/06 378/51 |
| 2003/0169847 A1 * | | 9/2003 | Karellas | A61B 6/481 378/98.3 |
| 2004/0005027 A1 | | 1/2004 | Nafstadius | |
| 2004/0228451 A1 * | | 11/2004 | Wu | A61B 6/583 378/207 |
| 2005/0017185 A1 * | | 1/2005 | King | G01T 3/08 250/370.05 |
| 2005/0094769 A1 * | | 5/2005 | Heismann | A61B 6/032 378/158 |
| 2005/0111619 A1 | | 5/2005 | Bijjani et al. | |
| 2005/0134203 A1 | | 6/2005 | Salop et al. | |
| 2006/0098773 A1 | | 5/2006 | Peschmann | |
| 2006/0140340 A1 * | | 6/2006 | Kravis | G01N 23/20 378/57 |
| 2006/0145083 A1 * | | 7/2006 | Miyata | G01T 1/2018 250/366 |
| 2006/0153330 A1 | | 7/2006 | Wong et al. | |
| 2006/0182326 A1 * | | 8/2006 | Schildkraut | A61N 5/1049 382/132 |
| 2006/0269049 A1 | | 11/2006 | Yin et al. | |
| 2007/0003009 A1 | | 1/2007 | Gray | |
| 2007/0003010 A1 * | | 1/2007 | Guertin | G21K 1/093 378/63 |
| 2007/0098142 A1 | | 5/2007 | Rothschild et al. | |
| 2007/0114426 A1 * | | 5/2007 | Tkaczyk | G01T 1/2018 250/370.09 |
| 2007/0165779 A1 | | 7/2007 | Chen et al. | |
| 2007/0215813 A1 | | 9/2007 | Whittum et al. | |
| 2007/0221869 A1 | | 9/2007 | Song | |
| 2007/0223650 A1 | | 9/2007 | Francke et al. | |
| 2007/0236300 A1 | | 10/2007 | Meddaugh et al. | |
| 2007/0237290 A1 * | | 10/2007 | Mostafavi | A61B 6/025 378/21 |
| 2007/0237304 A1 * | | 10/2007 | Nelson | A61N 5/1048 378/160 |
| 2007/0296530 A1 | | 12/2007 | Heisen et al. | |
| 2008/0123802 A1 * | | 5/2008 | Hirshenbein | G01N 23/04 378/5 |
| 2008/0156993 A1 * | | 7/2008 | Weinberg | A61B 6/12 250/363.03 |
| 2008/0205588 A1 | | 8/2008 | Kim | |
| 2008/0315106 A1 * | | 12/2008 | Buchinsky | A61B 6/032 250/370.09 |
| 2009/0010380 A1 * | | 1/2009 | Gotoh | A61B 6/032 378/5 |
| 2009/0067579 A1 * | | 3/2009 | Mansfield | A61N 5/10 378/189 |
| 2009/0135994 A1 * | | 5/2009 | Yu | A61B 6/032 378/5 |
| 2010/0066256 A1 | | 3/2010 | Meddaugh | |
| 2010/0316274 A1 * | | 12/2010 | Langheinrich | A61B 5/02007 382/130 |
| 2011/0282181 A1 * | | 11/2011 | Wang | A61B 5/0095 600/407 |

OTHER PUBLICATIONS

Final Office Action for U.S. Appl. No. 12/123,380 mailed on Apr. 13, 2011, 14 pages.
Non-Final Office Action for U.S. Appl. No. 12/123,380 mailed on Sep. 28, 2012, 12 pages.
Non-Final Office Action for U.S. Appl. No. 12/123,380 mailed on Oct. 26, 2010, 10 pages.
Advisory Action for U.S. Appl. No. 12/123,380 mailed on Jul. 6, 2011, 3 pages.
Notice of Allowance and Fees Due for U.S. Appl. No. 12/213,380 mailed on Dec. 16, 2013.

* cited by examiner

MULTI-ENERGY X-RAY IMAGING

RELATED APPLICATION DATA

This application is a divisional of U.S. patent application Ser. No. 12/123,380, filed on May 19, 2008, pending, the entire disclosure of which is expressly incorporated by reference herein.

BACKGROUND

This application relates generally to systems and methods for image acquisition and, more specifically, to systems and methods for acquiring and reconstructing multi-slice computed tomography data to produce high signal-to-noise ratio images with minimal metal-induced artifacts.

Computerized tomography (CT) involves the imaging of the internal structure of an object by collecting several projection images in a single scan or several scans, and is widely used in the medical field to view the internal structure of selected portions of the human body. Typically, several two-dimensional projections are made of the object, and a three-dimensional representation of the object is constructed from the projections using various tomographic reconstruction methods. In the case of electronic portal imaging, megavolt therapeutic X-rays can be used to generate images. However, this method results in images of low contrast and quality, in addition to incidentally damaging healthy tissue. As a result, imaging with megavoltage (MV) radiation is used primarily for portal verification, that is, to confirm that the treatment volume is being radiated.

In some cases, the optimal x-ray beam energy for maximizing signal-to-noise ratios and minimizing doses for in vivo computed tomography scans is in the range of 70-130 kV. This X-ray photon energy range is optimal for resolving soft tissue contrast in the CT images. However, at these beam energies, high density or highly attenuating objects such as gold fillings or metal prostheses can cause streaks and other image artifacts to be present in the projection images and in the final reconstructions.

Metal-induced artifacts may be compensated either by refinements to the CT system using anti-scatter grids, or by software corrections using iterative or interpolation techniques. However, software correction is problematic since it is computationally intensive and requires long reconstruction time, which may result in longer per-patient imaging processing time. Furthermore, software correction may be unavailable when imaging highly dense metal objects such as gold dental work or hip joint prostheses. In such cases, these highly dense metal objects completely absorb the primary x-ray beam thereby prevent absorption coefficient data from being obtained.

Sometimes, computed tomography systems may operate at much higher beam energies (e.g., up to 7 MV) than conventional diagnostic CT systems. Because the higher energy x-rays can penetrate metal objects, these higher energy CT systems produce images that are devoid of metal artifacts. However, as a trade off, patient radiation doses received from MV CT scans are often higher than those from a conventional kV CT scan. Moreover, the MV images exhibit significantly degraded soft-tissue contrast and spatial resolutions compared to kV images. The degradation in soft tissue contrast resolution at high beam energies is the inherent loss of differential contrast due to reduced photoelectric absorption and reduced Compton scattering cross-sections. Another reason for the degradation in soft tissue contrast resolution at high beam energies is reduced detective quantum efficiencies (DQE) due to the high penetration of the x-ray beam through the conventional detector conversion layers designed for kV x-rays. In some cases, the conventional detector's DQE may be as low as 3% under high beam energy, and thus the conventional detector is undesirable for imaging soft tissue at high beam energy. To effectively image soft tissues using high energy, high DQE detectors are required for high energy CT scans. However, high DQE detectors require very thick and expensive conversion layers to absorb the primary beam. Thus, building a large-area detector for high energy CT which can be used to scan a volume efficiently (e.g., in a single rotation of the source-detector pair) can be prohibitively expensive. On the other hand, imaging a target volume using only a high DQE detector with a small area is not desirable, because it would require many rotations to cover the axial extent of the volume of interest.

SUMMARY

In accordance with some embodiments, an imaging method includes obtaining a first image data for a subset of a target region, the subset of the target region having a first metallic object, obtaining a second image data for the target region, and using the first and second image data to determine a composite image.

In accordance with other embodiments, an imaging method includes obtaining information regarding a position of a first metallic object in a region of interest, and providing a radiation beam to irradiate a subset of the region of interest, the subset having the first metallic object.

In accordance with other embodiments, an imaging system includes a first detector configured to provide a first projection data using a first radiation having high energy, and a second detector configured to provide a second projection data using a second radiation having low energy, wherein the first detector has a first length, the second detector has a second length, and the first length is less than 75% of the second length.

In accordance with other embodiments, an imaging system includes an electronic portal imaging device, and a high detective quantum efficiency detector, wherein the high detective quantum efficiency detector has a first length, the electronic portal imaging device has a second length, and the first length is less than 75% of the second length.

In accordance with other embodiments, a system for use in an imaging procedure includes a processor configured to obtain information regarding a position of a first metallic object in a region of interest, and a collimator configured to shape a radiation beam based at least on the information regarding the position of the first metallic object.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present application, in which similar elements are referred to by common reference numerals. In order to better appreciate how advantages and objectives of the present application are obtained, a more particular description of the present application briefly described above will be rendered by reference to specific embodiments thereof, which are illustrated in the accompanying drawings. These drawings depict only typical embodiments and are not therefore to be considered limiting. The present application will be described and explained with additional specificity and detail through the use of the accompanying drawings in which.

DETAILED DESCRIPTION

Figure 1:
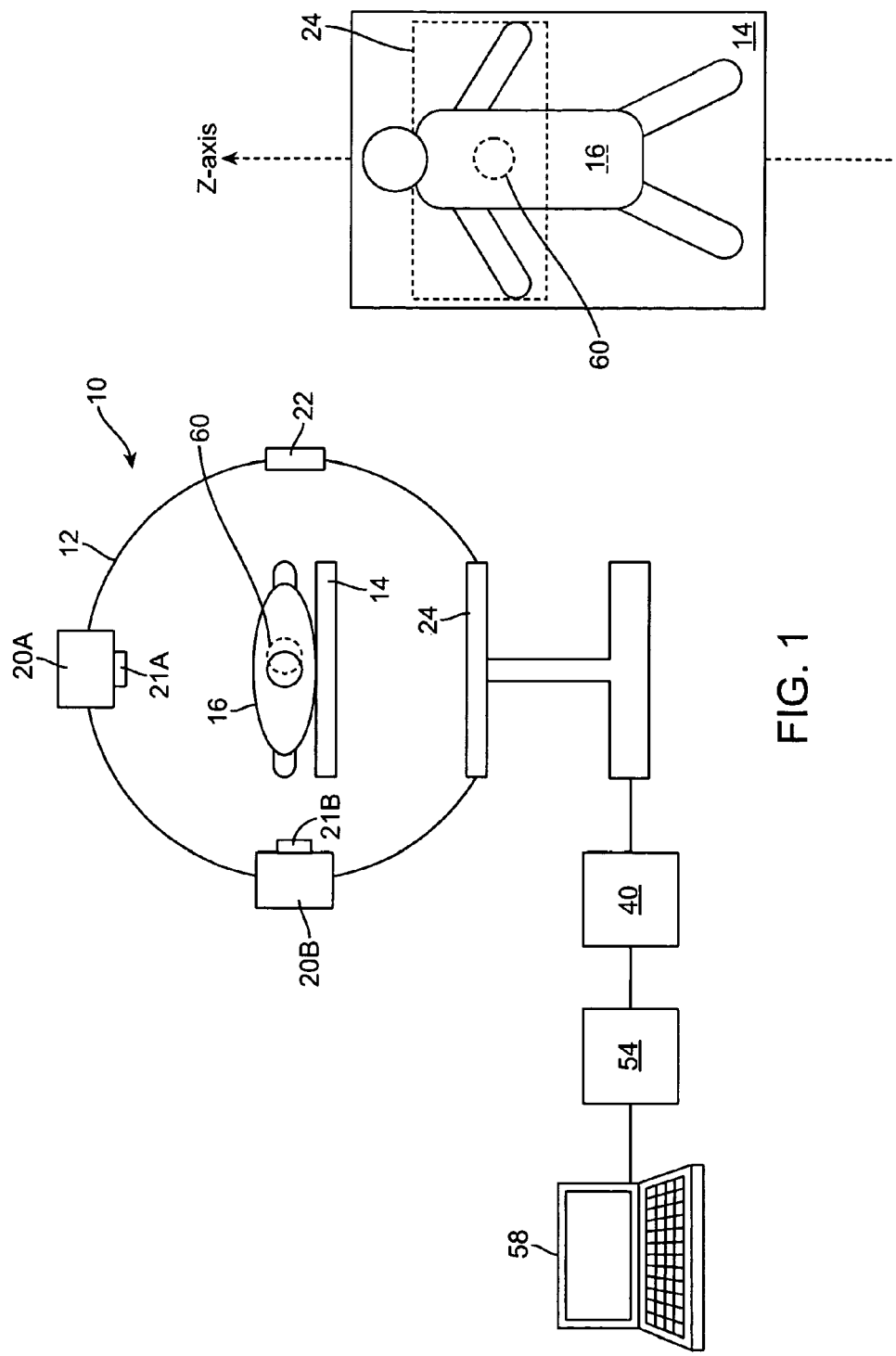
FIG. 1 illustrates an imaging system in accordance with some embodiments.

Various embodiments described hereinafter with reference to the figures. It should be noted that the figures are not drawn to scale and elements of similar structures or functions are represented by like reference numerals throughout the figures. It should also be noted that the figures are only intended to facilitate the description of embodiments. They are not intended as an exhaustive description of the invention or as a limitation on the scope of the invention. In addition, an aspect or a feature described in conjunction with a particular embodiment is not necessarily limited to that embodiment and can be practiced in any other embodiments.

This application describes systems and methods for acquiring and reconstructing projection data to produce high SNR images with minimal metal-induced artifacts. One embodiment describes a modification to an existing electronic portal imaging device (EPID) to allow for acquisition of megavoltage (MV) x-ray energy projection data using a high detective quantum efficiency (DQE) detector, targeting regions in the volume-of-interest where metal and other high density objects are present. The information from the high energy acquisition can be combined with information from lower energy acquisitions covering the larger volume to produce relatively artifact-free images with high contrast-to-noise ratios throughout the volume-of-interest. This approach allows for maximization of contrast and spatial resolutions while minimizing metal-induced artifacts, patient radiation dose, data acquisition times and costs. It also preserves the 2-D functionality of the EPID for patient positioning while expanding its utility by providing for CT acquisitions using detectors with high detective quantum efficiency.

System and Method of Multi-Energy Imaging

In one aspect, the present application includes methods and systems for generating a small image portion via a detector with high DQE (high DQE detector) and a remaining portion using another detector that is configured to receive low energy radiation beam. Such technology has the benefit of better image quality, minimal dose and scan time, and is cost effective. In one example, a high energy narrow-beam scan is performed in a subset of the field of interest where metal is present, and a low energy cone-beam or fan-beam scan that may cover the whole volume of interest is performed. The projection data from the high energy scan may be combined with projection data from the low energy scan to form a composite image.

In some embodiments, a high DQE detector for a high energy beam has approximately 5-90% detective quantum efficiency, and preferably has approximately 10-70% detective quantum efficiency. As used in the present application, the various x-ray beams may be stated as having specific "energies" or generally having energies in the kilovolt (kV) or megavolt (MV) range. It will be understood that this denotes the accelerating potential used to accelerate electrons in the device creating the beam, and not the resultant beam's energy. For example, in some embodiments, a radiation beam is considered to have a high energy level when it is produced using electrons accelerated at above 330 kV to strike a target. A radiation beam produced using electrons accelerated at less than or equal to 330 kV to strike a target is considered a low energy beam. In both cases, the resulting multi-spectral x-ray radiation beams have photons with different energies. However, the average energy of a "high energy" x-ray beam will be higher than the average energy of a "low energy" x-ray beam. It should be noted that the term "radiation beam" should not be limited to a beam that is generated using an accelerator, and that in other embodiments, the radiation beam may be generated using, e.g., an X-ray tube.

FIG. 1 illustrates an image acquisition system 10 in accordance with some embodiments of the present application. The system 10 includes a gantry 12, and a patient support 14 for supporting a patient 16. The system 10 also includes a first x-ray source assembly 20A mounted to the gantry 12 for projecting a beam of x-rays at a first energy, such as a fan beam, a cone beam, or a pencil beam, towards a first detector assembly 24 on opposite side of the gantry 12 while a portion of the patient 16 is positioned between the first x-ray source assembly 20A and the first detector assembly 24. The system 10 also includes a first collimator 21A to modulate the beam of x-rays. The system 10 further includes a second x-ray source assembly 20B that projects a beam of x-rays at a second energy, such as a fan beam, a cone beam, or a pencil beam, towards a second detector assembly 22 on opposite side of the gantry 12 while a portion of the patient 16 is positioned between the second x-ray source assembly 20B and the second detector assembly 22. The system 10 also includes a second collimator 21B to modulate the beam of x-rays. The first and second detector assemblies 24 and 22 each has a plurality of sensor elements configured for sensing a x-ray that passes through the patient 16. Each sensor element generates an electrical signal representative of an intensity of the x-ray beam as it passes through the patient 16. In some embodiments, the system 10 further includes a positioning system for moving the detector assembly 24, detector assembly 22, or both, in a direction that is perpendicular to a direction of the beam (e.g., axially along the z-axis).

The first x-ray source-detector pair (e.g., the first x-ray source assembly 20A and the first detector assembly 24) and the second x-ray source-detector pair (e.g., the second x-ray source assembly 20B and the second detector assembly 22) may be generally orthogonally positioned on the gantry 12. In other embodiments, the first and second x-ray source-detector pairs may be positioned relative to each other at other angles. In some embodiments, each x-ray source-detector pair may rotate independently from the other x-ray source-detector pair (e.g., by mounting them on separate rotating rings). Alternatively, the two pairs may be mounted to a single rotating ring.

In the illustrated embodiment, the first x-ray source assembly 20A is configured to deliver high energy x-ray beams, and the first detector assembly 24 is configured to generate image data in response to radiation at high energy levels; the second x-ray source assembly 20B is configured to deliver low energy x-ray beams, and the second detector assembly 22 is configured to generate projection data in response to radiation at low energy levels. In an alternative embodiment, the first x-ray source assembly 20A is configured to deliver low energy x-ray beams, and the first detector assembly 24 is configured to generate projection data in response to radiation at low energy levels; the second x-ray source assembly 20B is configured to deliver high energy x-ray beams, and the second detector assembly 22 is configured to generate image data in response to radiation at high energy levels.

The system 10 also includes a processor 54, a monitor 56 for displaying data, and an input device 58, such as a keyboard or a mouse, for inputting data. The processor 54 is coupled to a controller 40. The rotation of gantry 12 and the operation of the first and second x-ray source assemblies 20A and 20B are controlled by the controller 40, which provides power and timing signals to both x-ray source assemblies 20A and 20B and controls a rotational speed and position of the gantry 12 based on signals received from the processor 54. The controller 40 also controls an operation of the detector assembly 24. For example, the controller 40 can control a timing of when image signal/data are read out from the first detector assembly 24, and/or a manner in which image signal/data are read out from the first detector assembly 24. In some embodiments, the controller 40 (or a separate controller) controls the operation of the collimators 21A, 21B. Although the controller 40 is shown as a separate component from gantry 12 and the processor 54, in alternative embodiments, the controller 40 can be a part of the gantry 12 or the processor 54.

During a scan to acquire image data, the gantry 12 rotates about a region of interest 60 in the patient 16. While the gantry 12 rotates, the first x-ray source assembly 20A projects a beam of x-rays towards the first detector assembly 24 on opposite side of the gantry 12, and the second x-ray source assembly 20B projects another beam of x-rays towards the second detector assembly 22 on opposite side of the gantry 12. In one embodiment, the gantry 12 makes a 360° rotation around the region of interest 60 during projection data acquisition. Alternatively, if a full cone detector is used, the system 10 may acquire data while the gantry 12 rotates 180° plus the angle of the beam pattern (fan angle). Other angles of rotation may also be used, depending on the particular system being employed. In one embodiment, the first and second detector assemblies 24 and 22 are configured to collect sufficient amount of projection data for reconstruction of computed tomography images within one rotation (e.g., in one rotation or less) around the region of interest 60. In other embodiments, the assemblies 24, 22 may collect sufficient amount of projection data for reconstruction of computed tomography images in more than one rotation around the region of interest 60. In such cases, the first and second detector assemblies 24 and 22 may be configured to generate frames at slower rates.

In an exemplary embodiment, radiation treatment systems with an available kV imaging device, such as the Varian TRILOGY™, may be used to form part of the image acquisition system illustrated in FIG. 1. Such radiation treatment system has a treatment source for providing high energy beam, an electronic portal imaging device (EPID) that is situated 180 degrees opposite the treatment source for acquiring high energy images, and an available gantry mounted imager such as ON-BOARD IMAGER® from Varian (OBI) for receiving low energy beam and acquiring lower energy cone-beam images. The EPID is complemented by at least one strip of high DQE detector, which exemplifies one of the embodiments of the first detector assembly 24 in FIG. 1. The kV cone-beam projection acquisition may cover a large axial region (typically 15-30 cm) of the EPID. The strip of high DQE detector may complement a partial axial region of the EPID. For example, the high DQE detector may have at least one pixel row, and is less than 75% of the axial region of the EPID, preferably 1-35% of the axial region. The low energy, large area image acquisition may overlap with the high energy, narrower area image acquisition. The resulting signal is digitized and used to reconstruct 2-D projection radiographs (DPRs), which are typically used to verify patient positioning. The resulting signal may also be used to reconstruct 3-D cone-beam tomography images that are used to verify patient positioning or to generate radiotherapy treatment plans.

Figure 2:
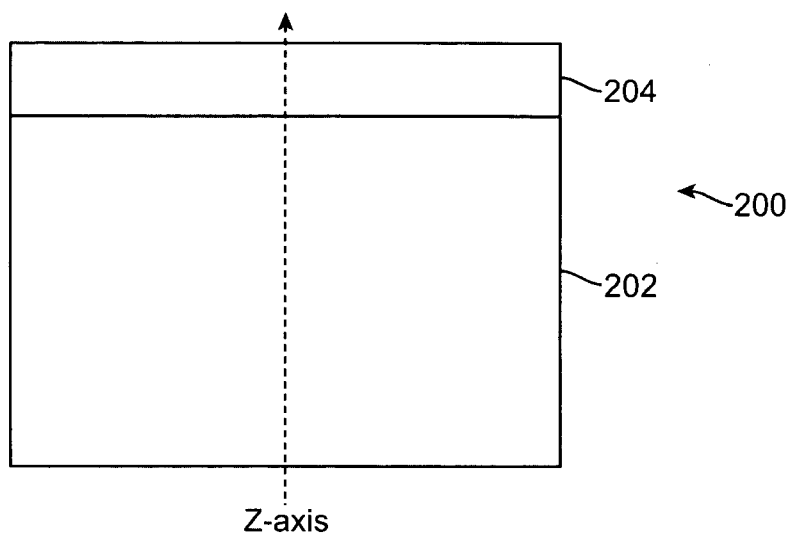
FIG. 2 illustrates an embodiment of a detector assembly.

FIG. 2 shows one of the embodiments of the first detector assembly 24 in FIG. 1. It should be noted that the first detector assembly 24 can have other configurations in other embodiments. The detector assembly 200 includes an EPID 202 and a high DQE detector 204, wherein the high DQE detector 204 has higher detective efficiency than the EPID 202. The EPID 202 includes an amorphous silicon flat panel detector that is covered with a thin layer of scintillator which, itself, is covered by a copper "build-up" plate. The build-up plate and scintillator convert x-ray photons into visible light photons that are detected using amorphous silicon photodiodes. In some embodiments, the high DQE detector 204 is an integral part of the EPID 202 and can be integrated into the EPID 202 at any part of the EPID 202. In another embodiment, the high DQE detector 204 and the EPID 202 are separate components. In the illustrated embodiments, the high DQE detector 204 is located at one end of the EPID 202. The high DQE detector 204 may be above, below, or next to (i.e., in a side-by-side configuration with) the EPID 202.

The high DQE detector 204 may be covered with cesium iodine (CsI) scintillator material or other scintillator material (e,g., GOS, $CdWO_4$, etc) with or without a metal build up plate, and may be made from a semiconductor detector such as CdTe or $HgI_2$. The high DQE detector 204 may alternatively be covered with a thick layer of photo conversion layer to maximize the absorption of incident X-rays. In the embodiment in which the high DQE detector 204 is above the EPID 202, since the high DQE detector 204 only partially covers a small surface area of the EPID 202, a very thick but smaller area of photo conversion layer can be used for the high DQE detector 204 without exceeding cost and weight constraints.

In the illustrated embodiments, the length of the high DQE detector 204 measured in the direction of the Z-axis is at most 75% of the length of the EPID 202, and more preferably less than 35% of the length of the EPID 202. In other embodiments, the length of the high DQE detector 204 may be characterized with respect to the second detector 22 instead of the EPID. For example, the length of the high DQE detector 204 measured in the direction of the Z-axis is at most 75% of the length of the second detector 22, and more preferably less than 35% of the length of the second detector 22.

Figure 3A:
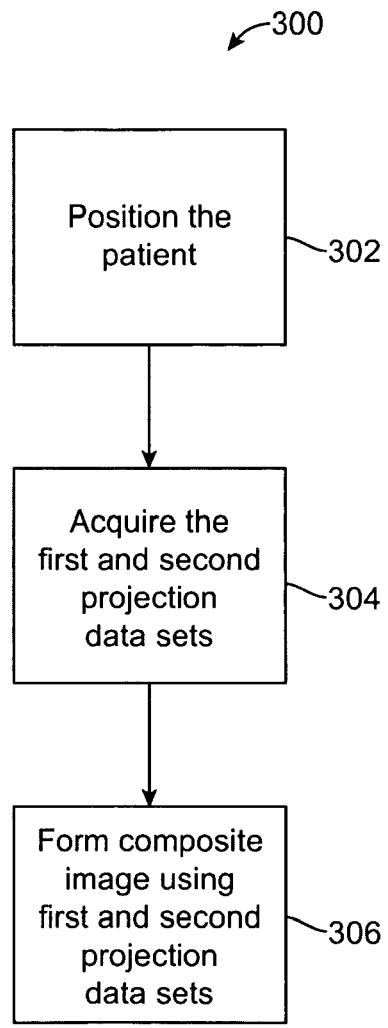
FIG. 3A illustrates a method of imaging a region of interest in accordance with some embodiments.
Figure 3B:
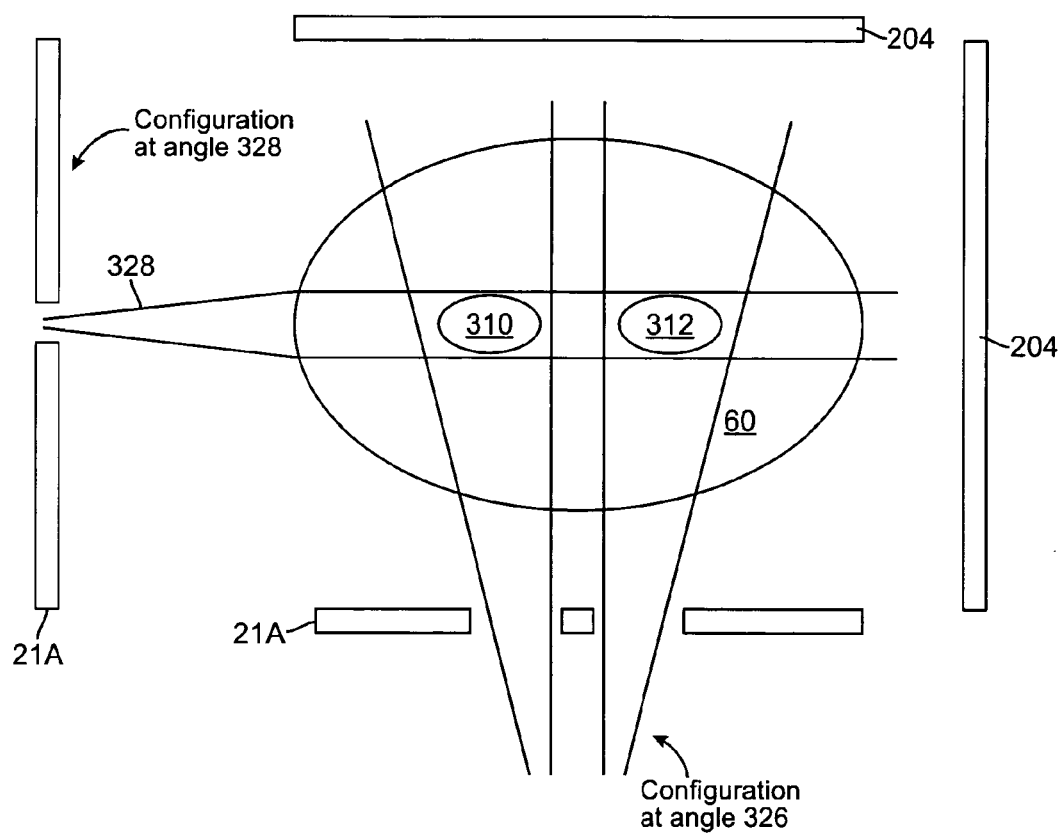
FIG. 3B illustrates an example of an operation of a collimator during a gantry rotation.

A method for imaging the region of interest 60 that contains metal object(s) using the system 10 is illustrated in FIGS. 3A-3B. In the illustrated example, the region of interest 60 contains two metal objects 310, 312. However, it is contemplated that in other cases, a region of interest may have one metal object, or more than two metal objects. Also, in other cases, the metal object(s) may have a shape that is different from that shown in the example. For example, the metal object may be fillings for teeth, metal prostheses, markers, etc.

First, the patient 16 is positioned such that the region of interest 60 can be imaged by the first and second detector assemblies 22, 24 (Step 302). In particular, the patient 16 is positioned such that (1) the region of interest 60 is between the second x-ray source assembly 20B and the second detector assembly 22, and (2) the subset of the region of interest 60 containing metal artifacts 310, 312 is between the first x-ray source assembly 20A and the high DQE detector 204 of the first detector assembly 24 (e.g., the subset is in the same isocenter plane as the high DQE detector 204).

Various techniques may be employed to accomplish the above conditions. In some embodiments, the patient support 14 may be moved axially so that the region of interest 60 can be targeted for image acquisition. In other embodiments, either or both of the first and second x-ray source assemblies 20A and 20B may be moved axially to align with the region of interest 60 of the patient 16 for image acquisition. Also, in other embodiments, either or both of the first and second detector assemblies 24 and 22 may be moved axially to align with the region of interest 60 of the patient 16 for image acquisition. In further embodiments, the first collimator 21A may be adjusted so that only the subset of the region of interest 60 containing metal artifacts 310, 312 is targeted for image acquisition through the first x-ray source assembly 20A and the first detector assembly 24. In other embodiments, any combination of the above may be used. For example, in other embodiments, adjusting the x-ray source assembly 20A and/or 20B, the detector assembly 22 and/or 24, the patient support 14, and/or the collimator 21A and/or 21B, may be performed to place the region of interest 60 of the patient 16 in a desired position for image acquisition.

The gantry 12 then rotates about the region of interest 60 once (completely, e.g., at least 360°, or partially, e.g., 180°) to acquire the first sets of projection data using the first detector assembly 24, and the second sets of projection data using the detector assembly 22 (Step 304). Various techniques may be used to obtain the first and second sets of projection data. In some embodiments, the first x-ray source 20A and the second x-ray source 20B alternates to emit high and low energy x-ray beams. The high energy radiation beams are attenuated by the subset of the region of interest 60 that contains the metal objects 310, 312, and impinges on the first detector assembly 24, and the low energy beams are attenuated by the region of interest 60 and impinges on the second detector assembly 22. The first detector assembly 24 then generates a first set of projection data, and the second detector 22 generates a second set of projection data.

In an alternative embodiment, the gantry 12 may rotate about the region of interest 60 more than once (a plurality of complete revolutions of gantry, e.g., each revolution is at least 360°, or a plurality of partial revolution of gantry, e.g., each revolution is 180°). In the first gantry rotation, the projection data for the region of interest 60 is acquired by using the low energy beams, and in the second gantry rotation, the projection data for a subset of the region of interest containing the metal objects 310, 312 is acquired by using the high energy beams. Alternatively, the high energy beams may be used in the first gantry rotation and the low energy beams may be used in the second gantry rotation.

It should be noted that the first and the second sets of image data should be generated while the object being imaged appears motionless. For example, when imaging a region of interest that is affected by breathing, the patient 16 can be instructed to hold breath while the gantry 12 is rotating about the region of interest 60 to collect image data. This ensures or increases the chance that the first set of image data can be correctly registered (in a spatial sense) with the second set of image data. For example, to increase the chance that the image data taken at the first and the second energy levels will have similar spatial registration, the image data are taken at the end of an expiration with breath holding. In other embodiments, the motion signal representative of the patient's breathing pattern may be obtained, and the motion signal can be synchronized with the image acquisition process such that image data are always obtained at a prescribed phase of a respiratory cycle.

In the illustrated embodiments, as the radiation source 20A is rotated about the patient 16 to obtain images at various gantry angles, the collimator 21A may be operated in synchronization with the rotation of the radiation source 20A. In such cases, in addition to using the collimator 21A to aim the radiation beam towards the high DQE detector 204 of the first detector assembly 24, the collimator 21A also tracks the metal objects 310, 312. FIG. 3B shows an example of an operation of the collimator 21A. As the gantry 12 rotates about the region of interest 60, the multi-leaf collimator (MLC) 21A can be adjusted to allow high energy x-ray to irradiate the region of interest that includes the metal objects 310, 312. For example, when gantry rotates to angle 326, the region of interest 60 contains two metal artifacts, 310 and 312. The MLC 21A is adjusted to have two openings to irradiate both metal artifacts 302 and 304. When the gantry 12 rotates to angle 328, both metal objects 310, 312 are in the same line of sight. Thus, the MLC 21A is adjusted to have one opening to irradiate both metal objects 310, 312. As illustrated, the adjustment is dynamic and is a function of view angles. In the above illustrated example, the collimator 21A is oriented such that the leaves of the collimator 21A are slidably positionable in a direction of the Z-axis. Such configuration allows the leaves of the collimator 21A to block and prevent radiation from reaching the EPID 202 (or most of the EPID 202), which allowing the leaves to modulate the beam to create one or more openings that correspond with the position of the metal objects. In other embodiments, the collimator 21A may be oriented in different angles.

In some embodiments, the image data obtained by the second detector 22 may be used to determine the positions of the metal objects 310, 312, and then the positional information is used to adjust the first collimator 21A such that the high energy beam can irradiate the metal objects 310, 312. Such may be accomplished using the processor 54 (or another processor), which receives the image data from the second detector 22, processes the image data to determine the positions of the metal objects 310, 312, and then transmits operation signals to the first collimator 21A to actuate various leaves of the collimator 21A.

Referring back to FIG. 3A, after the projection data for both radiation levels have been obtained, the projection data are then processed to create a composite image (Step 306). In some embodiments, projection data generated using radiation at the first and second energy levels are used to construct a first volumetric image and a second volumetric image, respectively. Various techniques can be used to construct a volumetric image. After the first and the second volumetric images are constructed, they are processed to obtain the composite image. In alternative embodiments, instead of creating the first and the second volumetric images, the first projection data and the second projection data can be processed to obtain composite projection data, and the composite projection data are then used to construct a volumetric image.

Various methods can be used to align the first image data with the second image data to create the composite image. In some embodiments, the first and the second projection data generated at the same gantry angles in one gantry rotation may be used to align the two sets of projection data. Similar data alignment techniques can also be applied when the first and the second sets of projection data are each generated at successive gantry rotations. In other embodiments, the first and the second image data are generated at different gantry angles. In such cases, the first image data and the second image data are used to create a first volumetric image and a second volumetric image, respectively. The first volumetric image can then be aligned with the second volumetric image by translating and/or rotating either of the first and the second volumetric images relative to the other, such that a feature in the first volumetric image aligns with the same feature in the second volumetric image.

Alternatively, an average shift in the gantry angle between the first image data and the second image data can be determined, and the average shift in the gantry angle can be used to align the first and the second volumetric images. In some embodiments, the average shift in the gantry angle between the first and second image data can also be taken into account when constructing either or both of the first and the second volumetric images such that the first and the second volumetric images are aligned. In other embodiments, the first image data can be modified to align with the second image data. For example, if first image data are generated at gantry angles=19° and 22° (measured from an arbitrary reference) using radiation at the first energy level, and second image data are generated at gantry angle=20° using radiation at the second energy level, then the first image data generated at gantry angles 19° and 21° can be processed (e.g., averaged, or interpolated) to obtain modified first image data that correspond to a gantry angle of 20°. The modified first image data and the second image data can then be used to generate a first volumetric image and a second volumetric image, respectively.

Various techniques may be used to combine kV and MV data in the scanning regions where there is overlap. One option is to use the MV projection data to modify or "correct" the kV projection data for rays where metal is present and use this information to minimize artifacts. In some embodiments, part(s) of the low energy image obtained may be substituted with image data from the high energy image obtained using the high DQE detector 204. For example, if portion of the image from the low energy detector contains artifacts resulted from the metal objects 310, 312, then that portion may be substituted with data from the high DQE 204. Alternatively (or in addition) separate reconstructions of the MV and kV data can be performed. The final images can be combined in a manner so that soft-tissue contrast and spatial resolutions are maximized but metal artifacts are minimized in the overlapping slices.

Other techniques for obtaining high energy and low energy images using the high DQE detector 204 and the low energy detector may be used. For example, when imaging the pelvis, it may be desirable to perform the high energy scans in the offset-detector mode to enlarge the transaxial field of view. This can be achieved by moving the portal imager laterally and performing a 360° rotation. A preferred embodiment is to perform the kV and MV acquisitions during the same rotation to maximize throughput. This is best achieved by interleaving the MV and kV pulses to minimize detected scatter radiation.

In some embodiments, the image obtained using the high DQE detector 204 may be stored for later use. For example, in some embodiments, the high energy image obtained using the high DQE detector 204 may be reused in one or more times— e.g., in different imaging sessions, which may be in the same day or in different days. The imaging sessions may be those that are performed for diagnostic purpose (e.g., for diagnosing the patient 16), for treatment planning, and/or for treatment purpose (e.g., for positioning patient 16 for the delivery of fractions at different times—e.g., different times in a day, or different days). Such technique is advantageous because by using the same high energy image in subsequent imaging session(s), the patient 16 does not need to be irradiated by high energy beam again to correct metal artifacts in these subsequent imaging session(s), thereby reducing radiation exposure to the patient 16. In other embodiments, instead of acquiring the high energy image only once, the high energy image may be acquired more than once, but sparingly through the course of the radiation treatment. For example, high energy images may be obtained in every other session, every other two sessions, or at other frequency. Alternatively, high energy image may be re-acquired if it is determined that there has been a change in a size, shape and/or a position (measured relative to surrounding tissue) of the target region 60. If high energy image is desired to be reused, the patient 16 should be positioned in the same location each time with respect to the high energy and low energy sources 21A, 21B, and detectors 204, 22. This ensures that the high energy image can be aligned with low energy image(s) that is obtained in subsequent imaging session(s).

Alternative Embodiments of Detector Assembly

Figure 4:
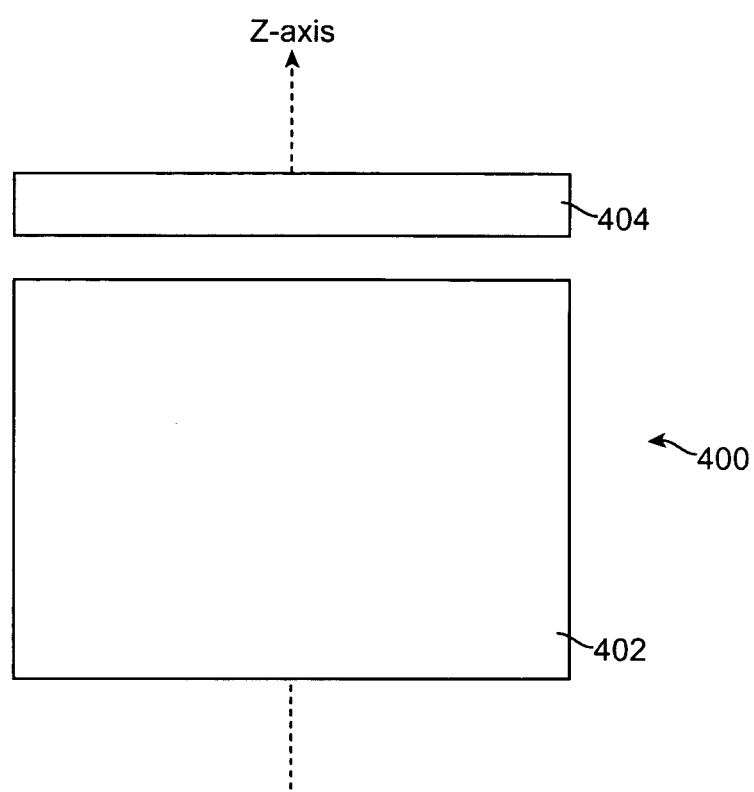
FIG. 4 illustrates another embodiment of a detector assembly.
Figure 5:
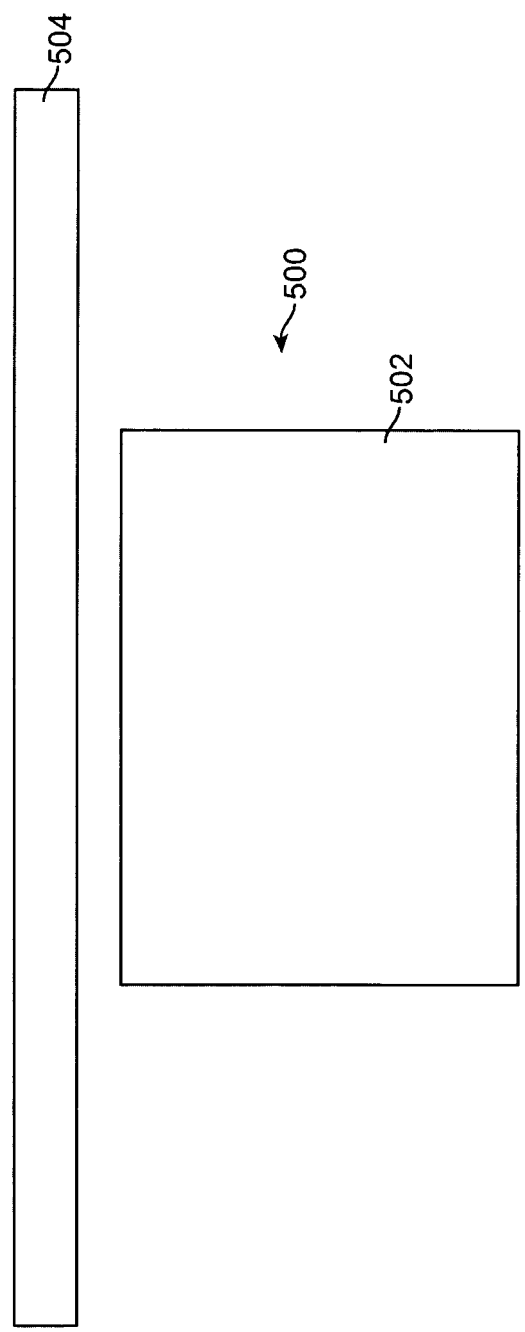
FIG. 5 illustrate another embodiment of a detector assembly.
Figure 6:
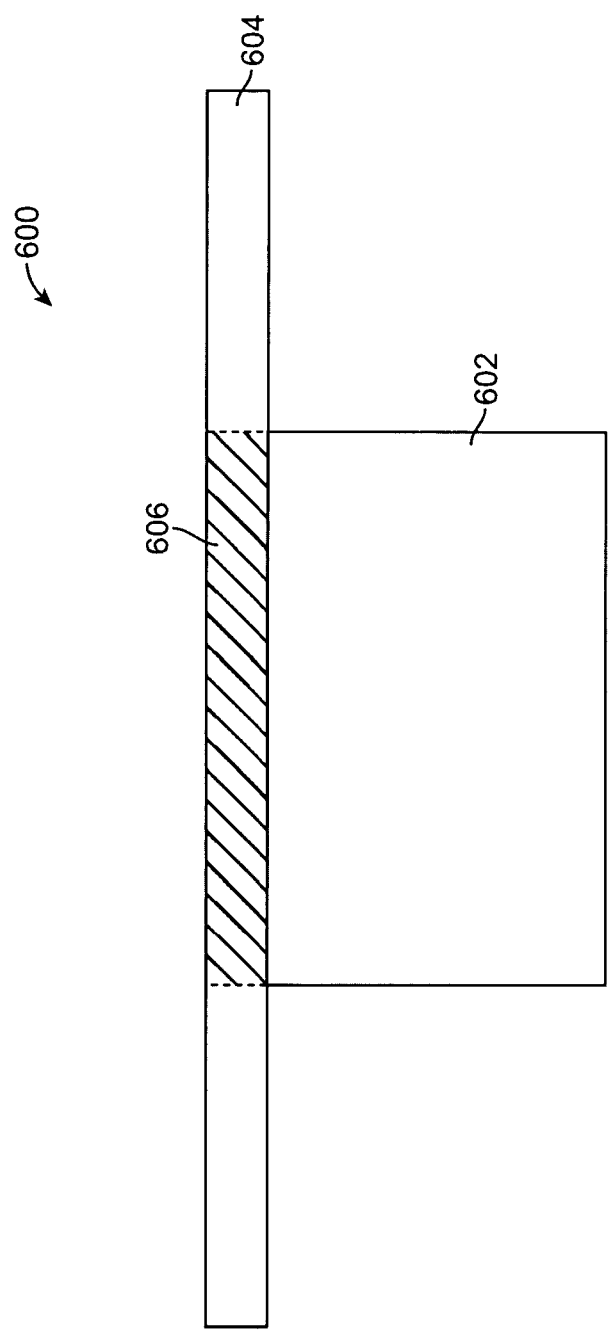
FIG. 6 illustrates another embodiment of a detector assembly.

It should be noted that the first detector assembly 24 can have other configurations in other embodiments, such as different sizes, lengths, widths, and shapes. FIG. 4, FIG. 5, and FIG. 6, each shows an exemplary embodiment of the first detector assembly 24 of FIG. 1.

In FIG. 4, the detector assembly 400 includes a high DQE detector 404 and an EPID 402. The high DQE detector 404 may have separate electronics from the EPID 402 and be placed adjacent to the EPID 402. FIG. 5 and FIG. 6 show a technique of expanding the transaxial field of view by using a separate high DQE detector wider than the EPID.

In FIG. 5, the detector assembly 500 includes an EPID 502 and a high DQE detector 504. The high DQE detector 504 is placed adjacent to the EPID 502, and is wider than the EPID in width. The high DQE detector 504 may have an extension on one end having a width up to 50% width of the EPID, or alternatively, may have an extension on each end having a width up to 50% width of the EPID. The high DQE detector 504 may be a wholly integrated unit, or alternatively, a plurality of detector elements connected together. In an alternative embodiment, the detector elements that extend beyond the EPID 502 may be arranged to be moved, by e.g., sliding, pivoting, or folding into a more compact shape, when the EPID 502 is stowed, or when expanded transaxial view is not required.

In FIG. 6, another alternative embodiment of the detector assembly 600 is shown, which includes an EPID 602 and a high DQE detector 604. The high DQE detector 604 is placed adjacent to the EPID 602, and may partially overlap a portion of the EPID 602. The portion of the EPID 602 that overlaps with the high DQE detector 604 is covered with a strip conversion layer 606 to reduce circuitry. The high DQE detector 604 may be wider than the EPID 602 in width to providing a wider transaxial field of view. The high DQE detector 604 may have an extension on one end having a width up to 50% width of the EPID, or alternatively, may have an extension on each end having a width up to 50% width of the EPID. The high DQE detector 604 may be a wholly integrated unit, or alternatively, a plurality of detector elements connected together. In the alternative embodiment, the detector elements that extend beyond the EPID 602 may be arranged to be moved, e.g., by sliding, pivoting, or folding into a more compact shape, when the EPID 602 is stowed, or when expanded transaxial view is not required.

Figure 7A:
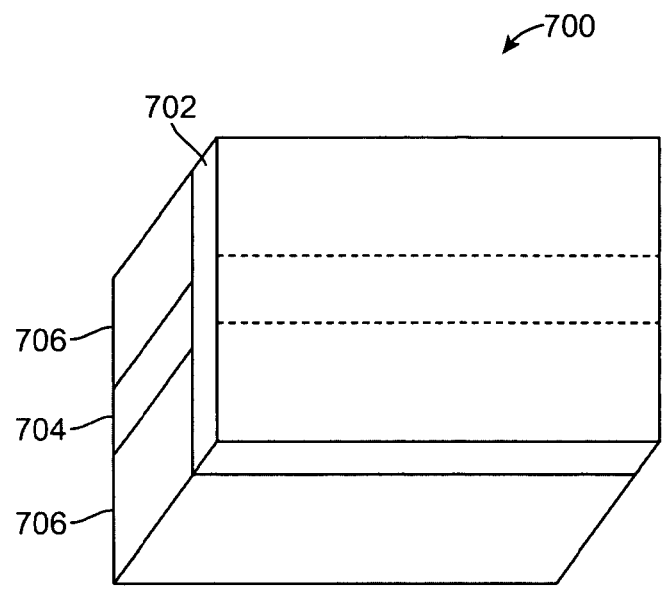
FIGS. 7A and 7B illustrate another embodiment of a detector assembly.
Figure 7B:
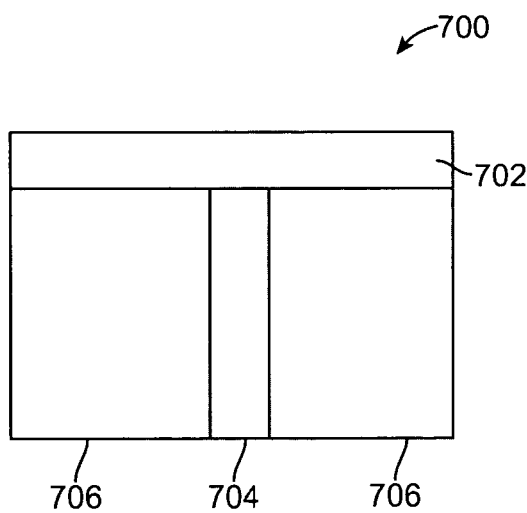

FIG. 7A and FIG. 7B show an alternative embodiment of the detector assembly 24 of FIG. 1, where the high DQE detector is placed underneath the EPID. FIG. 7A shows the top view of the detector assembly 700, which includes an EPID 702 and a high DQE detector 704. The high DQE detector 704 is positioned underneath the EPID 702. FIG. 7B shows the side view of the detector assembly 700. The EPID 702 is mounted on a glass substrate 706 and the high DQE detector 704 is integrated into the glass substrate. The detector 704 and the EPID 702 may share the same readout circuitry, or can alternatively have its own dedicated readout circuitry. Alternatively, the high DQE detector 704 may be placed on its own glass substrate underneath the EPID 702. The advantage of placing the detector 704 beneath the EPID 702 is that it preserves the full functionality of the EPID 702. Furthermore, attenuation of the high energy x-ray signal to be detected by the high DQE detector 704 when transmitting through the EPID 702 is minimal since high energy x-ray is highly transmittable through the EPID 702. To achieve uniform backscatter below the EPID, backscatter compensation material may be placed beside the high DQE strip detector with similar or equal backscatter properties as the high DQE strip detector.

Figure 8:
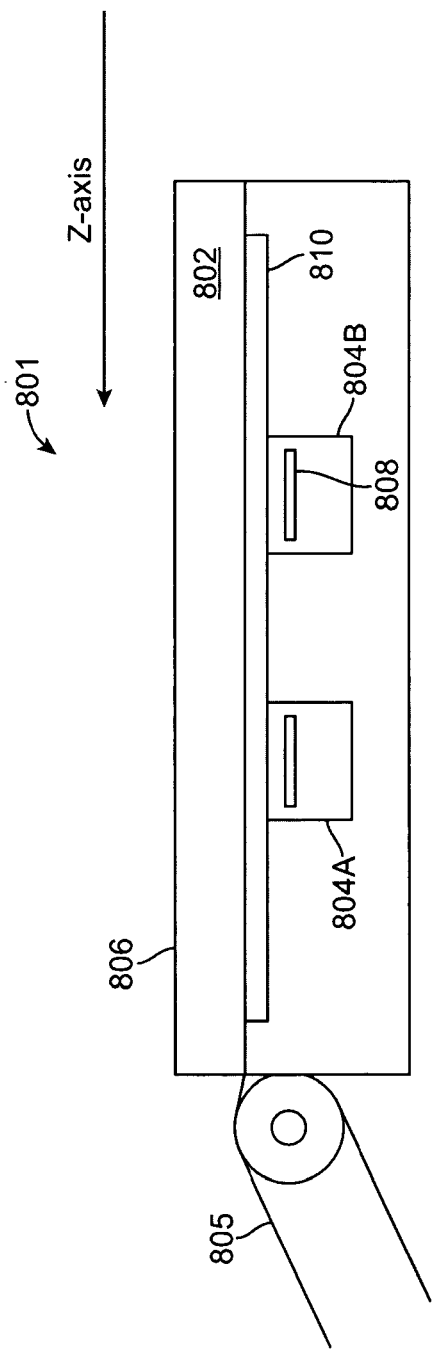
FIG. 8 illustrates an embodiment of a detector assembly having a rail system.

FIG. 8 shows another embodiment of the detector assembly. In this embodiment, the detector assembly 801 includes an EPID 802, two high DQE detectors 804A and 804B, and a rail system 810 disposed within a cover 806. The rail may be straight, or curved, e.g., such that the beams incident on the DQE detectors are perpendicular to the surface of the high DQE detectors. The position of the detector assembly 801 is controlled by a control arm 805 to move the detector assembly to the target imaging area. The high DQE detectors 804A and 804B are disposed underneath the EPID 802 and attached to the rail system 810, where the detectors 804A and 804B can move axially along the Z-axis of the EPID 802. A sheet of TFT 808 is disposed within each detector 804A and 804B and in close proximity to the EPID 802. During imaging, the detectors 804A and 804B may move axially along the Z-axis of the EPID 802 to be positioned on the line of sight of the high energy beam impinging on the metal artifacts in the region of interest. As gantry angle changes, the MLC and the detectors 804A and 804B are dynamically repositioned so that the detectors are on the line of sight of the high energy beam to capture the imaging data for a subset of the target region 60 that includes the metal objects. In other embodiments, the configuration in FIG. 8 may have more than two high DQE detectors, wherein some of the detectors may be stationary and some may be part of the rail system.

The imaging system 10 should not be limited to the configuration discussed previously, and may have other configurations in other embodiments. For example, in any of the embodiments described herein, the imaging system 10 may not include the EPID 202. In such cases, the high DQE detector 204 is not integrated with, nor is it located next to any EPID.

In further embodiments, the radiation source 20A may be a multi-energy radiation source that is capable of providing high energy and low energy radiation beams. In such cases, the second radiation source 20B is not needed, and the detector assemblies 22, 24 may be moveable relative to the radiation source 20A so that the radiation source 20A may be selectively in operative positions with the detector assemblies 22, 24. During use, the radiation source 20A are the second detector assembly 22 are placed in operative position relative to each other (e.g., by rotating the radiation source 20A or the first detector assembly 24), so that they can be used to obtain image data for the region of interest 60 using low energy radiation beam. The radiation source 20A and the first detector assembly 24 are then placed in operative position relative to each other (e.g., by rotating the radiation source 20A or the first detector assembly 24), so that they can be used to obtain image data for the subset of the region of interest 60 that contain metal object(s) using high energy radiation beam.

Also, in any of the embodiments described herein, the high DQE detector is coupled or located next to the low energy detector assembly 22 (e.g., an OBI) instead of the EPID. For examples, the high DQE detector may overlap part of the second detector assembly 22, may be located underneath the second detector assembly 22, or may be located next to the second detector assembly 22 in a side-by-side configuration. The high DQE detector may be a separate component from the second detector assembly 22, or alternatively, be integrated with the second detector assembly 22 to form a single imager. In these embodiments, the low energy and high energy x-ray sources 20A, 20B may be coupled together, in close proximity of each other, or be integrated as a single multi-energy source. During use, the detector assembly 22 and the high DQE may be shifted to selectively place them in operative positions with the x-ray source(s). Alternatively, or additionally, the collimator may be used to selectively direct the beam to the high DQE or the detector assembly 22. Other methods as those similarly described herein may also be used.

It should be further noted that the high DQE detector may not be in a form of a strip. In other embodiments, the high DQE detector may be shaped like rectangle, circle, oval, or any other shapes that are suitable for image acquisition. Also, instead of the examples of the dimension described previously, the high DQE detector may have different dimensions and sizes in other embodiments. In some embodiments, the high DQE detector has at least one pixel row and less than 75% of the surface area of the EPID, and preferably less than 50% of the surface area of the EPID, and even more preferably, less than 20% of the surface area of the EPID.

Also, in further embodiments, the high DQE detector needs not be arranged relative to the EPID along the Z-axis. In other embodiments, the high DQE detector may be located relative to the EPID such that the high DQE detector is offset away from the Z-axis. For example, the lengthwise axis of the high DQE may be parallel to the Z-axis.

Construction of High DQE Detector

In some embodiments, the high DQE detector includes an x-ray conversion layer made from a scintillator element, such as Cesium Iodide (CsI), and a photo detector array (e.g., a photodiode layer) coupled to the x-ray conversion layer. Other examples of scintillator materials that may be used include cadmium tungstate ($CdWO_4$) and BGO (bismuth germanate) (formula: $Bi_4Ge_3O_{12}$). These are both higher density materials which allow the scintillator layer to be made less thick for the same x-ray absorbtion. This can be an advantage when fabricating the high DQE strip—e.g., for the scintillator sub-elements or blocks of the high DQE detector 204. Alternatively, a photoconductor can be used to replace the conventional scintillator—photodiode configuration. The x-ray conversion layer generates light photons in response to x-ray radiation, and the photo detector array, which includes a plurality of detector elements, is configured to generate electrical signal in response to the light photons from the x-ray conversion layer. The photo detector array can be made from a variety of materials, such as Mercuric Iodide ($HgI_2$), Lead Iodide ($PbI_2$), Bismuth Iodide ($BiI_3$), Thallium Bromide (TlBr), Cesium Iodide (CsI), Cadmium Zinc Telluride (CdZnTe), Cadium Telluride (CdTe), Amorphous Selenium (a-Se), or equivalent thereof. $HgI_2$ and $PbI_2$ are particularly preferred because photoconductors made from these materials can increase the modulation transfer function (MTF) value—a measure of spatial resolution, thereby providing high radiograph quality. Other materials known in the art may also be used. The photoconductor may be a single or polycrystalline layer, or an amorphous layer.

In order to minimize optical cross-talk which causes loss of spatial resolution, the high DQE detector may be composed of a series of separate blocks of the scintillator material. The blocks may be, for example, 0.784 mm×0.784 mm×30 mm high. For example, the blocks may be sized to match the effective pixel pitch of the current TRILOGY™ EPID. However, the transverse dimensions of the scintillator blocks may be varied to suit finer or coarser pixel pitches, and different EPID panels. The height dimension of the blocks may be adjusted to suit different incident X-ray photon energies, and to trade off the X-ray absorption efficiency against light transmission, weight, and cost.

The scintillator blocks are coated with opaque reflective material on as many as five sides. In some embodiments, the bottom face of the block is not coated with reflective material. The light emitted when the scintillator absorbs an X-ray photon, is thereby trapped within the individual scintillator block and escapes only through the bottom of the block to illuminate the photodiode(s) of the pixel(s) immediately beneath the block. The opaque reflective coating, which prevents light leaking to adjacent blocks, may be a diffuse, white, reflective material or a mirror-like, specularly reflective material, e.g., aluminum. The several faces of the scintillator block may be coated with a mixture of diffuse and specularly reflective materials in order to maximize the efficiency with which light photons generated within the block are internally reflected and transported to the photodiode underneath. In other embodiments, a partly reflective layer is applied to the bottom surface of the block in order to reduce the intensity of light reaching the photodiode.

In a preferred embodiment, the individual scintillator blocks are packed together, side by side, similar to bricks in a wall, to form a layer for the high DQE detector. The thin reflective coatings on the sides of adjacent blocks touch each other back-to-back, somewhat resembling the mortar between bricks.

The high DQE detector may have a radiation receiving surface that is rectangular in shape. The radiation receiving surface may have a dimension that is, for example, 40 cm×2 cm. These dimensions may vary in different embodiments. The long axis of the high DQE detector preferably lies in the transverse direction to the Z-axis of the EPID. Since the distance from the target of the accelerator to the EPID is of the order of 150 cm and the ends of the thick scintillator strip are off center, e.g., displaced 20 cm from the centerline of the MV fan beam, the incident X-ray photons may intersect the ends of the strip at an angle. Since the individual scintillator blocks may be several centimeters in height, one X-ray photon may intersect multiple scintillator blocks at the ends of the DQE strip. This spreads the signal across multiple pixels and degrades the spatial resolution.

Figure 9:
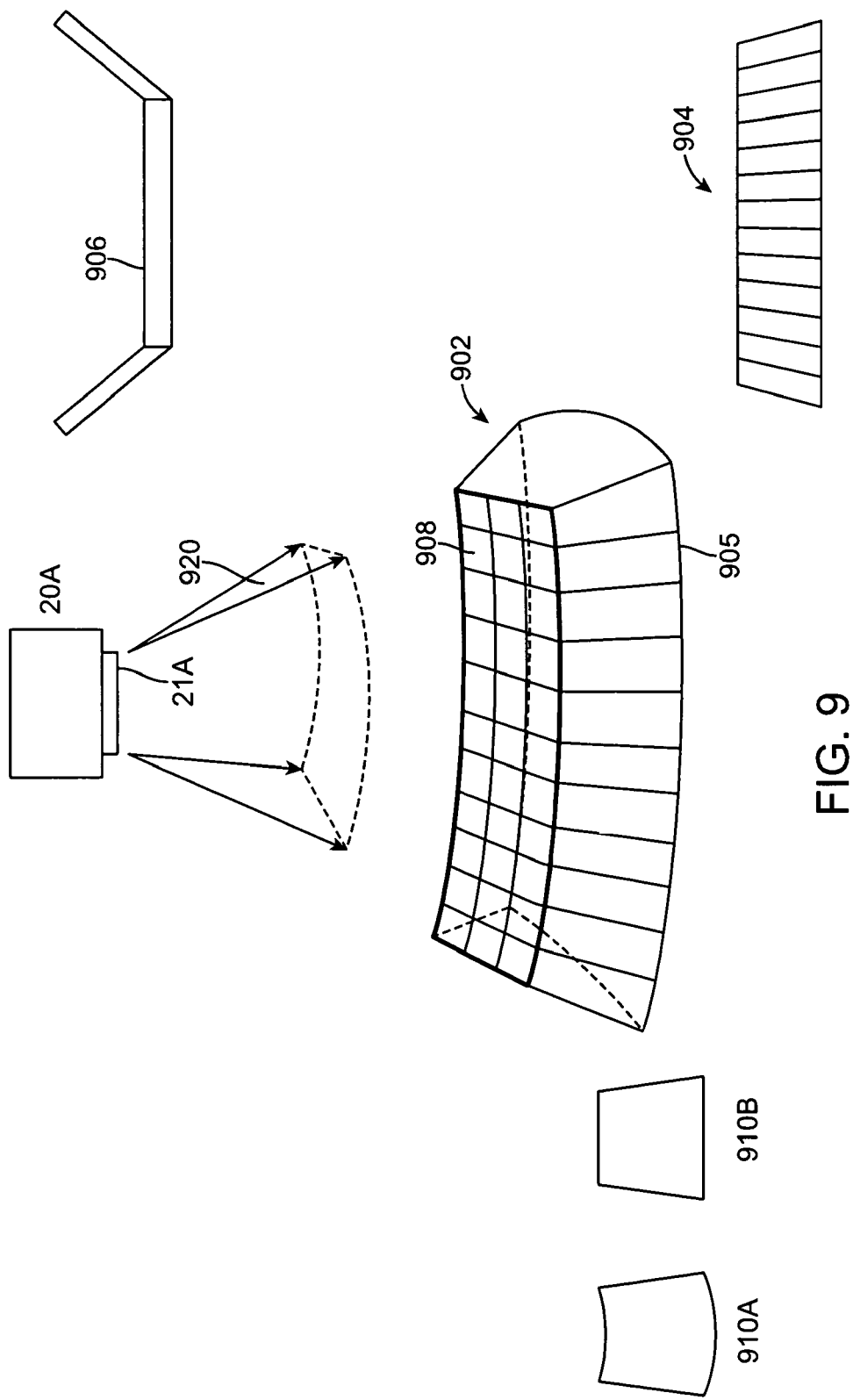
FIG. 9 illustrates another embodiment of a detector assembly.

In order to correct for this effect, the off center scintillator blocks may be shaped so that they are not rectangular prisms but, instead, two of the opposite faces are tapered in towards each other. The scintillator blocks can be shaped in such a way that individual blocks still pack closely together but they are increasingly angled over as the distance from the center of the strip increases. FIG. 9 illustrates a high DQE detector 902 that embodies such concept. The high DQE detector 902 may be a component of the detector 24 in FIG. 1. The high DQE detector 902 includes a plurality of imaging elements 905, generally in a truncated wedge shape, and may have a curvilinear surface (e.g., an arc). In this embodiment, the high DQE detector 902 preferably has a shape that generally correlates with the shape of the fan beam 920. In some embodiments, the width-wise side view of the off-center scintillator blocks has a shape that is similar to a truncated wedge (910A). In other embodiments, the width-wise side view of the off-center scintillator blocks has a shape that is similar to a parallelogram or a trapezoid (910B). The plurality of imaging elements 905 have respective radiation receiving surfaces 908 that collectively form a radiation receiving surface for the high DQE detector 902. The imaging elements 905 may be arranged in such a way that individual elements are packed closely together but increasingly angled away from the center of the detector as the distance from the center of the detector increases (e.g., like an arc). Such configuration is beneficial in that each of the imaging elements 905 of the detector 902 is located substantially the same distance from the x-ray source assembly 20A and able to capture more image data from the scattering nature of the fan beam and further scattering of the x-ray beam after being attenuated. In other embodiments, the detector 902 may have a relatively rectilinear middle portion, and side portions that are tapered (thereby forming a trapezoid configuration 904) or curved (thereby forming an arc) at the two sides of the detector 902. In further embodiments, the detector 902 may have a rectilinear surface or a surface having other profiles.

In the above embodiment, the individual imaging elements 905 are tapered in the direction along the long axis of the scintillator strip, in order to compensate for the off-axis angle of the incident X-ray photons. In other embodiments, the high DQE detector 902 may be longer along the direction of z-axis than that shown in the figure. In such configuration, the imaging elements 905 may be tapered on four side faces so that they are also angled in the direction along the axis of the CT system.

In other embodiments, the high DQE detector 902 may have other configurations. For example, in other embodiments, the high DQE detector may have the configuration shown as 906. In this configuration each scintillator block faces towards the target and the incident X-ray photons pass through a single scintillator block, even at the ends of the scintillator strip. This preserves the spatial resolution at the ends of the strip. Also, in this embodiment, the high DQE detector 902 has a mid portion, and two side portions that form angles relative to the mid portion. In some cases, the side portions may rotate relative to the mid portion, thereby allowing the high DQE detector 902 to be folded into a compact configuration.

Figure 10:
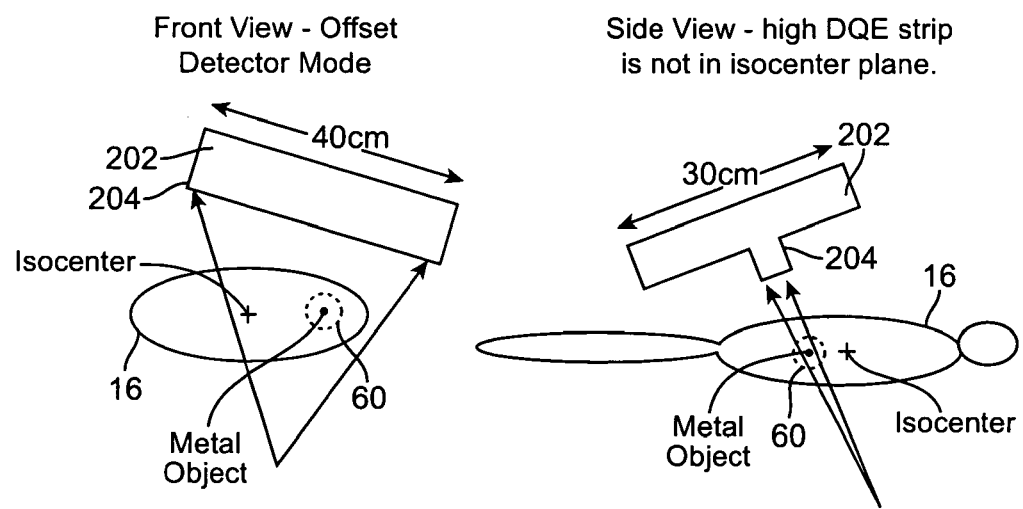
FIG. 10 illustrates another embodiment of a detector assembly that is capable of tilting in one or more axes.

In some embodiments, it may be desirable to shift the imaging devices laterally (transaxially) in order to sufficiently sample a wide target region through the course of a 360 degree scan (FIG. 10—left figure). This is known as offset-detector or half-fan mode. In such cases, both the low energy and high energy detectors 22, 24 are capable of performing this shift. Moreover, to maintain best focus it may be desired to tilt the detector 22/24 to point towards the source. In other embodiments, it may be desirable to tilt along a second axis, e.g., when the high DQE strip is situated in the isocenter plane (FIG. 10—right figure).

Computer System Architecture

Figure 11:
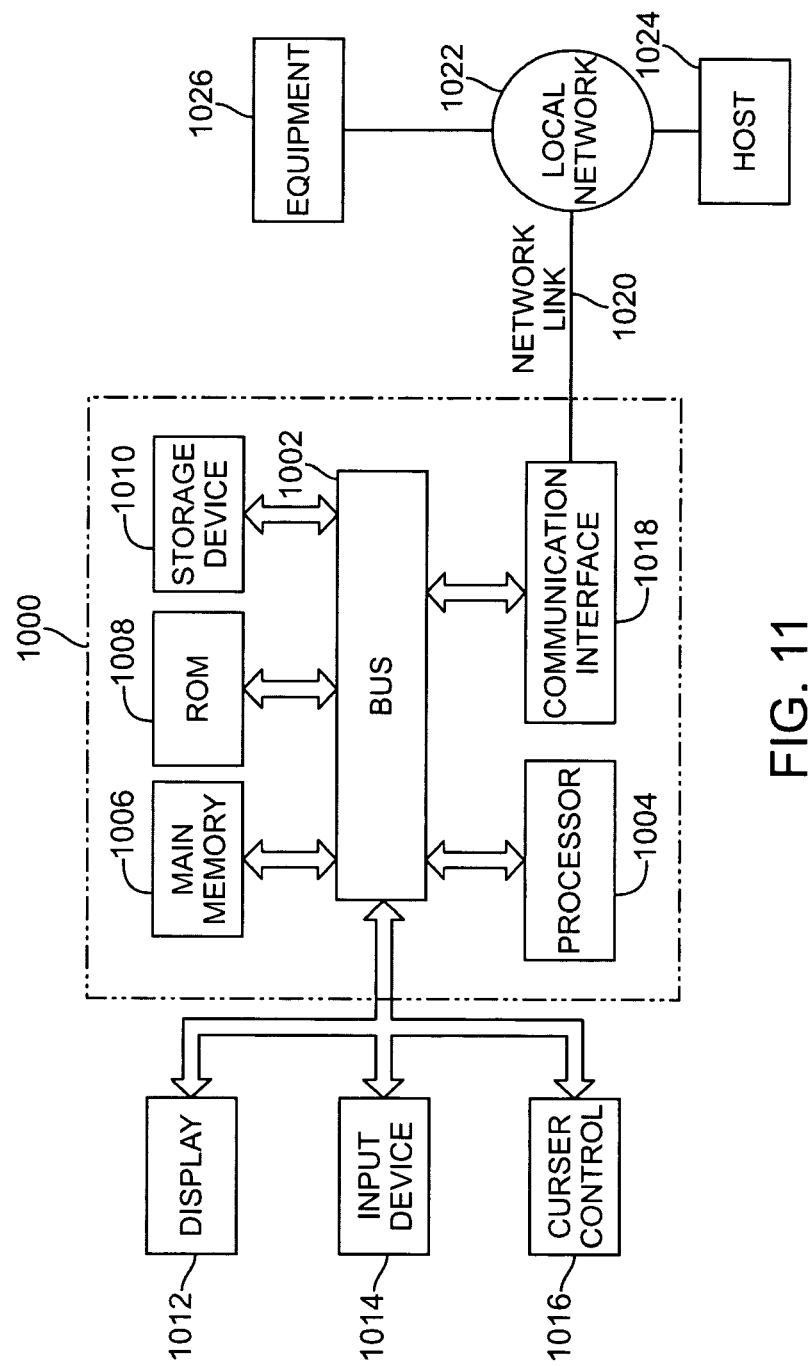
FIG. 11 illustrates a block diagram of a computer system.

FIG. 11 is a block diagram of a computer system 1000 that may be used to implement various embodiments described herein. Computer system 1000 includes a bus 1002 or other communication mechanism for communicating information, and a processor 1004 coupled with the bus 1002 for processing information. The processor 1004 may be an example of the processor 54, or alternatively, an example of a component of the processor 54, of FIG. 1. The computer system 1000 also includes a main memory 1006, such as a random access memory (RAM) or other dynamic storage device, coupled to the bus 1002 for storing information and instructions to be executed by the processor 1004. The main memory 1006 also may be used for storing temporary variables or other intermediate information during execution of instructions to be executed by the processor 1004. The computer system 1000 further includes a read only memory (ROM) 1008 or other static storage device coupled to the bus 1002 for storing static information and instructions for the processor 1004. A data storage device 1010, such as a magnetic disk or optical disk, is provided and coupled to the bus 1002 for storing information and instructions.

The computer system 1000 may be coupled via the bus 1002 to a display 1012, such as a cathode ray tube (CRT), for displaying information to a user. An input device 1014, including alphanumeric and other keys, is coupled to the bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane.

This application is related to the use of computer system 1000 for collecting and processing image data. According to one embodiment of the application, such use is provided by computer system 1000 in response to processor 1004 executing one or more sequences of one or more instructions contained in the main memory 1006. Such instructions may be read into the main memory 1006 from another computer-readable medium, such as storage device 1010. Execution of the sequences of instructions contained in the main memory 1006 causes the processor 1004 to perform the process steps described herein. One or more processors in a multi-processing arrangement may also be employed to execute the sequences of instructions contained in the main memory 1006. In alternative embodiments, hard-wired circuitry may be used in place of or in combination with software instructions to implement the application. Thus, embodiments of the application are not limited to any specific combination of hardware circuitry and software.

The term "computer-readable medium" as used herein refers to any medium that participates in providing instructions to the processor 1004 for execution. Such a medium may take many forms, including but not limited to, non-volatile media, volatile media, and transmission media. Non-volatile media includes, for example, optical or magnetic disks, such as the storage device 1010. Volatile media includes dynamic memory, such as the main memory 1006. Transmission media includes coaxial cables, copper wire and fiber optics, including the wires of which the bus 1002 is composed. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 54 for execution. For example, the instructions may initially be carried on a magnetic disk of a remote computer. The remote computer can load the instructions into its dynamic memory and send the instructions over a telephone line using a modem. A modem local to the computer system 1000 can receive the data on the telephone line and use an infrared transmitter to convert the data to an infrared signal. An infrared detector coupled to the bus 1002 can receive the data carried in the infrared signal and place the data on the bus 1002. The bus 1002 carries the data to the main memory 1006, from which the processor 1004 retrieves and executes the instructions. The instructions received by the main memory 1006 may optionally be stored on the storage device 1010 either before or after execution by the processor 1004.

The computer system 1000 also includes a communication interface 1018 coupled to the bus 1002. The communication interface 1018 provides a two-way data communication coupling to a network link 1020 that is connected to a local network 1022. For example, the communication interface 1018 may be an integrated services digital network (ISDN) card or a modem to provide a data communication connection to a corresponding type of telephone line. As another example, the communication interface 1018 may be a local area network (LAN) card to provide a data communication connection to a compatible LAN. Wireless links may also be implemented. In any such implementation, the communication interface 1018 sends and receives electrical, electromagnetic or optical signals that carry data streams representing various types of information.

The network link 1020 typically provides data communication through one or more networks to other devices. For example, the network link 1020 may provide a connection through local network 1022 to a host computer 924 or to an equipment 1026. The data streams transported over the network link 1020 can include electrical, electromagnetic or optical signals. The signals through the various networks and the signals on the network link 1020 and through the communication interface 1018, which carry data to and from the computer system 1000, are exemplary forms of carrier waves transporting the information. The computer system 1000 can send messages and receive data, including program code, through the network(s), the network link 1020, and the communication interface 1018.

Although particular embodiments of the present application have been shown and described, it will be understood that it is not intended to limit the present application to the preferred embodiments, and it will be obvious to those skilled in the art that various changes and modifications may be made without departing from the spirit and scope of the present application. For example, the operations performed by the processor 54 can be performed by any combination of hardware and software within the scope of the application, and should not be limited to particular embodiments having a particular definition of "processor". In addition, the term "image" as used in this specification includes image data that may be stored in circuitry or a computer-readable medium, and should not be limited to image data that is displayed visually. The specification and drawings are, accordingly, to be regarded in an illustrative rather than restrictive sense. The present application is intended to cover alternatives, modifications, and equivalents, which may be included within the spirit and scope of the present application as described herein.

What is claimed is:

1. An imaging system, comprising:
   a first detector configured to provide a first projection data using a first radiation having high energy; and
   a second detector configured to provide a second projection data using a second radiation having low energy;
   wherein the first detector has a first length, the second detector has a second length, and the first length is less than 75% of the second length; and
   wherein the first detector has a first imaging plane and the second detector has a second imaging plane that corresponds with the first imaging plane.

2. The imaging system of claim 1, wherein the first length is less than 35% of the second length.

3. The imaging system of claim 1, wherein the first detector comprises a plurality of high detective quantum efficiency detector elements.

4. The imaging system of claim 1, further comprising a third detector.

5. The imaging system of claim 4, wherein the first and third detectors collectively form a single imager.

6. The imaging system of claim 4, wherein the first detector at least partially overlaps the third detector.

7. The imaging system of claim 4, wherein the first detector is disposed underneath the third detector.

8. The imaging system of claim 4, wherein the first and third detectors are tiltable.

9. The imaging system of claim 1, wherein the first detector is moveable along a Z-axis of the imaging system.

10. The imaging system of claim 9, wherein one or both of the first and second detectors are moveable along a X-axis of the imaging system.

11. The imaging system of claim 9, wherein the second detector is moveable along the Z-axis of the imaging system.

12. The imaging system of claim 1, wherein the first radiation is in a form of a beam, and the imaging system further comprises a collimator for changing a shape of the beam.

13. The imaging system of 12, wherein the collimator is configured to change the shape of the beam such that the beam irradiates a subset of a region of interest, the subset having one or more metallic objects.

14. The imaging system of claim 1, wherein the first detector comprises a photo detector array coupled to an x-ray conversion layer.

15. The imaging system of claim 1, wherein the first detector comprises a photoconductor layer.

16. The imaging system of claim 1, wherein the first imaging plane is parallel to the second imaging plane.

17. The imaging system of claim 1, wherein the first detector and the second detector are both configured to face a same direction for a given imaging position.

18. The imaging system of claim 1, wherein the first length of the first detector is parallel to the first imaging plane, and wherein the second length of the second detector is parallel to the second imaging plane.

19. An imaging system, comprising:
   a first detector configured to provide a first projection data using a first radiation having high energy; and
   a second detector configured to provide a second projection data using a second radiation having low energy; and
   a third detector;
   wherein the first detector has a first length, the second detector has a second length, and the first length is less than 75% of the second length; and
   wherein the first detector has a width that is 50% to 100% wider than the third detector.

20. The imaging system of claim 19, wherein the first length of the first detector is parallel to a first imaging plane of the first detector, and wherein the second length of the second detector is parallel to a second imaging plane of the second detector.

21. An imaging system, comprising:
   a first detector configured to provide a first projection data using a first radiation having high energy; and
   a second detector configured to provide a second projection data using a second radiation having low energy; and
   a third detector;
   wherein the first detector has a first length, the second detector has a second length, and the first length is less than 75% of the second length; and
   wherein the third detector comprises an EPID.

22. The imaging system of claim 21, wherein the first length of the first detector is parallel to a first imaging plane of the first detector, and wherein the second length of the second detector is parallel to a second imaging plane of the second detector.

23. An imaging system, comprising:
   a first detector configured to provide a first projection data using a first radiation having high energy; and
   a second detector configured to provide a second projection data using a second radiation having low energy;
   wherein the first detector has a first length, the second detector has a second length, and the first length is less than 75% of the second length; and
   wherein the second detector comprises an OBI.

24. An imaging system, comprising:
   an electronic portal imaging device; and
   a high detective quantum efficiency detector;
   wherein the high detective quantum efficiency detector has a first length, the electronic portal imaging device has a second length, and the first length is less than 75% of the second length.

25. The imaging system of claim 24, wherein the high detective quantum efficiency detector overlaps a portion of the electronic portal imaging device.

26. The imaging system of claim 24, wherein the high detective quantum efficiency detector is underneath the electronic portal imaging device.

27. The imaging system of claim 24, wherein the high detective quantum efficiency detector and the electronic portal imaging device are integrated together to form a single imager.

28. The imaging system of claim 24, wherein the electronic portal imaging device has a first imaging plane and the high detective quantum efficiency detector has a second imaging plane that corresponds with the first imaging plane.

29. The imaging system of claim 28, wherein the first imaging plane is parallel to the second imaging plane.

30. The imaging system of claim 28, wherein the electronic portal imaging device and the high detective quantum efficiency detector are both configured to face a same direction for a given imaging position.

31. The imaging system of claim 24, wherein the first length of the high detective quantum efficiency detector is parallel to a first imaging plane of the high detective quantum efficiency detector, and wherein the second length of the electronic portal imaging device is parallel to a second imaging plane of the electronic portal imaging device.

* * * * *